United States Patent [19]

Rozovsky et al.

[11] 4,415,477
[45] Nov. 15, 1983

[54] CATALYST FOR DEHYDROGENATION OXYGEN-CONTAINING DERIVATIVES OF THE CYCLOHEXANE SERIES INTO THE CORRESPONDING CYCLIC KETONES AND/OR PHENOLS

[76] Inventors: Alexandr Y. Rozovsky, Rublevskoe shosse, 97, korpus 3, kv. 25; Valentin D. Stytsenko, ulitsa Musy Dzhalilya, 34, korpus 2, kv. 18; Svetlana A. Nizova, ulitsa Volgina, 27, kv. 144; Petr S. Belov, ulitsa Vavilova, 52, korpus 3, kv. 163; Alexandr J. Dyakonov, ulitsa Begovaya, 32, kv. 71, all of Moscow, U.S.S.R.

[21] Appl. No.: 219,170

[22] Filed: Dec. 22, 1980

[30] Foreign Application Priority Data

Dec. 27, 1979 [SU] U.S.S.R. ............... 2852801
Dec. 27, 1979 [SU] U.S.S.R. ............... 2852803

[51] Int. Cl.³ .............. B01J 23/78; B01J 23/74; B01J 27/02; B01J 27/08
[52] U.S. Cl. .................... 502/178; 568/361; 568/763; 568/799; 502/213; 502/215; 502/218; 502/227; 502/242; 502/263; 502/337
[58] Field of Search ............ 252/472, 473, 459, 440, 252/443, 455 R

[56] References Cited

U.S. PATENT DOCUMENTS

| | | | |
|---|---|---|---|
| 3,399,132 | 8/1968 | Mulaskey | 252/459 |
| 3,480,531 | 11/1969 | Mulaskey | 252/472 |
| 3,691,102 | 9/1972 | Swift | 252/472 |
| 3,886,091 | 5/1975 | Bertus | 252/440 |
| 4,363,750 | 12/1982 | Rozovsky et al. | 252/459 |

*Primary Examiner*—P. E. Konopka
*Attorney, Agent, or Firm*—Ladas & Parry

[57] ABSTRACT

The herein-proposed catalyst for dehydrogenation oxygen-containing derivatives of the cyclohexane series having the following general formula

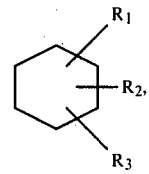

where
$R_1$ is either hydrogen or alkyl $C_1$-$C_4$,
$R_2$ and $R_3$ are radicals having either the same or different values —H, —OH, =O, provided that $R_2$ and $R_3$ are not hydrogen atoms both at a time,
$R_1$, $R_2$, $R_3$ being linked to different carbon atoms of the ring to form the corresponding cyclic ketones and/or phenols, comprises the following components (wt. %):
nickel—15 to 55
tin—0.2 to 1.95
inert carrier—84.8 to 43.05,
while the atomic ratio of nickel and tin lies within 15:1 and 410:1, respectively, and may contain additionally an alkali salt of a mineral acid in an amount of 0.01 to 1.0 wt. %.

2 Claims, No Drawings

CATALYST FOR DEHYDROGENATION OXYGEN-CONTAINING DERIVATIVES OF THE CYCLOHEXANE SERIES INTO THE CORRESPONDING CYCLIC KETONES AND/OR PHENOLS

INDUSTRIAL APPLICABILITY OF THE INVENTION

The present invention relates to the field of catalytic transformations of organic compounds and has particular reference to catalysts for dehydrogenation of oxygen-containing derivatives of the cyclohexane series into the corresponding cyclic ketones and/or phenols, and to processes for dehydrogenating such oxygen-containing derivatives of the cyclohexane series into the corresponding cyclic ketones and/or phenols with the use of said catalysts.

Dehydrogenation of oxygen-containing derivatives of cyclohexane is one of the cardinal petrochemical processes. To cite but certain of these one may point to dehydrogenation of cyclohexanol into cyclohexanone which is an intermediate of large-scale caprolactam production, or dehydrogenation of cyclohexanol into phenol, one of the most important products of chemical industry, or else dehydrogenation of cyclohexanediol-1,2 into pyrocatechol, an intermediate product for producing highly efficient additives to petroleum products and polymers. All the afore-discussed processes are carried out in the presence of heterogeneous catalysts, which as a rule are the metal of Group VIII of the Periodic System, or copper, supported by inert contact carriers.

BACKGROUND OF THE INVENTION

One prior catalyst for dehydrogenating oxygen-containing derivatives of cyclohexane is known to comprise nickel as an active component, as well as promoters, viz., copper, chromium and sodium sulphate, on an inert contact carrier (cf. U.S. Pat. No. 2,640,084, class 260/621, 1953). However, this catalyst features but low capacity in dehydrogenating monooxygen cyclohexane derivatives, such as cyclohexanol or cyclohexanone, i.e., the productivity for the end product, viz, phenol is not more than 0.15 kg per liter catalyst at 350° C.

Moreover, when dehydrogenating cyclohexane derivatives containing more than one oxygen atom per molecule in the presence of the abovesaid catalyst, a secondary process, i.e., dehydration occurs to a substantial extent. As a result, the selectivity of the catalyst involved with respect to the desired dihydric phenols in, say, dehydrogenating cyclohexanediol-1,2 into pyrocatechol, is as low as 15 to 20 percent.

One more catalyst for dehydrogenating oxygen-containing derivatives of the cyclohexane series having the following general formula

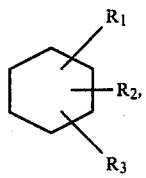

where
$R_1$ is either hydrogen or alkyl $C_1$–$C_4$,
$R_2$ and $R_3$ are radicals having either the same or different values —H, —OH, =O, provided that $R_2$ and $R_3$ cannot both be hydrogen,
$R_1$, $R_2$, $R_3$ being linked to different carbon atoms of the ring into the corresponding ketones and phenols, said catalyst containing, as an active component, a metal of Group VIII of the periodic system, such as nickel, as well as a promoter, i.e., tin and an inert contact carrier, i.e., silica. The atomic ratio of the metal of Group VIII and tin in this catalyst ranges within 1.7:1 to 15:1, respectively. The weight percentage content of the aforesaid catalyst components lies within the following limits:

metal of Group VIII of the Periodic System—2 to 20
tin—2 to 30
inert carrier—to make up 100 percent
(cf. H. E. Swift, J. E. Bozik, J. Catal, v.12, p.5 /1968/; U.S. Pat. No. 3,580,970, class 260-621H, 1971).

The above catalyst has the disadvantage of having only a low capacity with respect to ketones and phenols and in being insufficiently stable. Thus, for instance, the productivity for phenol of an optimum-composition nickel-tin catalyst (atomic ratio of Ni:Sn being 2.5:1) supported on silica equals 1.3 kg/l at 375° C., whereas in eight hours the productivity drops below 1.0 kg/l (cf. FIG. 4 of the afore-cited U.S. Patent). Similar results have been obtained in the study by M. Masai et al. (J. Catal, v.38, p.128, 1975), i.e., the initial productivity of a nickel-tin catalyst (Ni:Sn ratio being 2.5:1) in cyclohexanone dehydrogenation at 400° C. equals 1.0 kg/l, whereas in eight hours it drops to only 0.6 kg/l.

Selectivity of the known catalyst in dehydrogenating mono-oxygen derivatives of cyclohexane into phenol is reasonably high, amounting to 98 percent, whereas the selectivity for ketones is rather low. Thus, when dehydrogenating cyclohexanol into cyclohexanone the abovesaid selectivity is as low as 50 percent (cf. op. cit. by H. E. Swift and J. E. Bozik). Especially low is the selectivity of the known catalyst when it is applied for dehydrogenating polyfunctional oxygen-containing derivatives of the cyclohexane series into the corresponding polyhydric phenols. For instance, when dehydrogenating cyclohexandiol-1,2 at 330° C. and below, the selectivity in terms of the desired pyrocatechol is as low as 30 percent, whereas dehydrogenation process occurring at a temperature above 330° C. are accompanied by vigourously running secondary reactions, which result in fast deactivation of the catalyst.

A process for dehydrogenating oxygen-containing derivatives of the cycolohexane series of the aforesaid general formula (feed stock) into the corresponding cyclic ketones and/or phenols is known to comprise contacting such oxygen-containing derivatives of the cyclohexane series with the nickel-tin catalyst of the abovesaid composition at a temperature of from 375° to 400° C. in the presence of hydrogen taken in a sixfold molar excess amount with respect to the feed stock (cf. H. E. Swift, J. E. Bozik, J. Catal., v.12, p.5, 1968; U.S. Pat. No. 3,580,970, class 260-621H, 1971).

The afore-noticed disadvantages of the known nickel-tin catalyst account for the disadvantages of a process for dehydrogenating oxygen-containing compounds of the cyclohexane series using said catalyst. Thus, e.g., use of a low-capacity catalyst results in low output of the entire dehydrogenation process, while inadequate stability of the catalyst affects adversely all characteristics of the process, that is, conversion of the starting materials, selectivity and yield of the end products with time, and is responsible for a necessity of periodically stopping the dehydrogenation process for regenerating the catalyst.

With a view to improving the stability of the known catalyst, its composition incorporates additionally such a deficient and costly element as platinum, as well as chromium and sodium sulphate. However, this badly affects the catalyst capacity and the productivity of the whole process, which is as low as 0.2 kg/l per hour.

SUMMARY OF THE INVENTION

It is an object of the present invention to provide a catalyst for dehydrogenating oxygen-containing derivatives of the cyclohexane series of the aforesaid general formula, into the corresponding cyclic ketones and/or phenols, which would be featured by high capacity, selectivity and stability characteristics.

It is another object of the present invention to provide a process for dehydrogenating oxygen-containing derivatives of the cyclohexane series, which would enable one to produce the corresponding cyclic ketones and/or phenols at high yields and output.

According to said and other objects the invention consists in the development of a catalyst for dehydrogenating oxygen-containing derivatives of the cyclohexane series having the following general formula

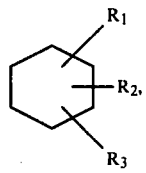

where
$R_1$ is either hydrogen or alkyl $C_1$–$C_4$,
$R_2$ and $R_3$ are radicals having either the same or different values —H, —OH, =O, provided that $R_2$ and $R_3$ cannot both be hydrogen atoms,
$R_1$, $R_2$, $R_3$ being linked to different carbon atoms of the ring, into the corresponding cyclic ketones and/or phenols, said catalyst containing an active component, nickel, a promoter, tin, both as free metals and an inert carrier, i.e., silica, diatomite, silicon carbide, or magnesia, wherein, according to the present invention, the weight percentage content of said components lies within the following limits:
nickel—15 to 55
tin—0.2 to 1.95
inert carrier—84.8 to 43.05,
while the atomic ratio of nickel and tin lies within 15:1 and 410:1, respectively.

A catalyst containing 15 to 55 wt. % of nickel on the aforesaid inert carrier is considered to have a maximum capacity. With the nickel content below 15 wt. % the catalyst capacity drops drastically, while the nickel content higher than 55 wt. % is inexpedient inasmuch as it fails to improve useful catalyst properties.

For the aforesaid nickel content, the aimed selectivity and stability of the proposed catalyst are attained due to the use of a promoter, i.e., tin taken in an amount of from 0.2 to 1.95 percent of the catalyst weight, the atomic ratio of nickel and tin must be within 15:1 to 410:1. With the tin content below 0.2 wt. % and the atomic ratio of Ni:Sn above 410:1 the desired catalyst is featured by low selectivity and stability when applied to dehydrogenate oxygen-containing derivatives of the cyclohexane series, and the dehydrogenation process is accompanied by undesirable secondary processes of dehydration and condensation, whereby the catalyst is liable to rapid coking and deactivation. With the tin content above 1.95 wt. % and the atomic ratio of Ni:Sn below 15:1 the catalyst capacity is badly affected, especially in the reaction of the formation of phenols.

With a view to increasing the selectivity and productivity of the desired catalyst for dehydrogenating oxygen-containing derivatives of the cyclohexane series at elevated (above 300° C.) temperatures, the composition of the catalyst is recommended to contain an alkali salt of a mineral acid in an amount of from 0.1 to 1.0 wt. %. The cations of such salts may be represented by, say, lithium, potassium, sodium, calcium, barium, while the anions, by a chloride, sulphate, fluoride, sulphide, phosphate, etc. The lower quantitative limit of the aforesaid salt additive corresponds to a minimum concentration of the additive to the catalyst, which provides for higher selectivity and capacity thereof. With the content of the above alkali salt of a mineral acid higher than 1.0 wt. % the catalyst capacity is drastically reduced.

The present invention has for its subject matter also a process for dehydrogenating oxygen-containing derivatives of the cyclohexane series having the afore-stated general formula, into the corresponding cyclic ketones and/or phenols using the proposed catalyst. According to the present process, the oxygen-containing derivatives of the cyclohexane series (i.e., the feed stock) is contacted with the proposed catalyst, according to the present invention, in the presence of a diluent, i.e., an inert gas, aliphatic hydrocarbons $C_1$–$C_4$, nitrogen, carbon-dioxide gas, steam, aliphatic alcohols $C_1$–$C_3$, or various combinations thereof at a temperature of from 160° to 340° C. and a partial pressure of the oxygen-containing derivatives of the cyclohexane series ranging between 0.003 and 0.1 atm, at feed rates of said oxygen-containing derivatives of the cyclohexane series and said diluent from 0.5 to 5.0 kg/l.hr and from 1 to 53 m³/l. .hr, respectively.

The function of the diluent is to increase the equilibrium yield of the desired hydrogenation products. Inasmuch as this process is a reversible one and is accompanied by an increased number of molecules involved, dilution of the original oxygen-containing derivative of the cyclohexane series to partial pressures within 0.003 to 0.1 atm will add to the yield of the end product.

In order to attain high yield of the proposed dehydrogenation process, it is necessary to feed the original stock at a high rate ranging within 0.5 and 5.0 kg/l.hr. Nevertheless, the proposed dehydrogenation process may be carried out with the feed rates coming beyond the abovespecified range; however, with the feed rate below 0.5 kg/l per hour the catalyst exhibits but too low productivity, whereas with the feed rate above 5.0 kg/l per hour the degree of conversion of the oxygen-containing derivatives of the cyclohexane series is as low as 70 percent, which impedes isolation of the end products from the catalysate. In keeping with the abovesaid values of the stock feed rate and the requirements to the degree of the stock dilution, the range of the feed rates of the diluent is established to be within 1 to 53 m³/l per hour.

The present dehydrogenation process may run also at temperatures below 160° or above 340° C.; however, in the former case the reaction mixture consists by more than 80 percent of the unreacted stock after having been in contact with the catalyst, which hampers isolation of the desired ketones and/or phenols, while in the latter case the reaction is accompanied by appreciable secondary processes of dehydration and coking resulting in formation of condensation products that deactivate the catalyst.

Thus, it has been found quite unexpectedly that the proposed catalyst containing small additives of tin to nickel, i.e., 0.2 to 1.95 wt. % and the atomic ratio of Ni:Sn being from 15:1 and higher, when applied in a process for dehydrogenation of oxygen-containing derivatives of the cyclohexane series, features high productivity (up to 3.8 kg/l per hour), selectivity (up to 99 percent) and stability. These characteristics remain invariable upon a prolonged period of the catalyst operation, amounting to at least 400 hours. The catalyst enables dehydrogenation of oxygen-containing derivatives of the cyclohexane series into the corresponding ketones (at 200° C. and below), phenols (at 240° C. and above), or mixtures thereof.

It is worth noting that, unlike the heretofore-known nickel-based catalysts, the present catalyst makes it possible to effect highly selective (up to 94 percent) dehydrogenation of polyoxygen derivatives of the cyclohexane series into the corresponding polyhydric phenols, e.g., cyclohexanediol-1,2 into pyrocatechol. In addition, the proposed catalyst also differs from the known nickel-containing catalysts in that it is capable of stable dehydrogenation of oxygen-containing organic compounds in the atmosphere of steam and is resistant to deterioration by admixtures of sulphur-bearing compounds that may occur in the reaction mixture.

One more favourable and advantageous feature of the present catalyst is its rather simple composition, incorporating such inexpensive and readily available metals as nickel and tin. The proposed catalyst is prepared following conventional techniques using routine process equipment.

Practical application of the herein-disclosed catalyst has made it possible to carry out a highly productive process for dehydrogenating oxygen-containing derivatives of the cyclohexane series into the corresponding ketones and/or phenols, viz, the productivity of the catalyst with respect to ketones, mono- and polyhydric phenols ranges within 3.4 to 3.8 kg/l per hour, while its selectivity for ketones, phenol and polyhydric phenols makes up 97 to 99 percent with practically complete transformation of the starting reactants, which considerably facilitates the isolation of the end products from the reaction mixture and practice of environmental protection measures.

Of no less importance is the fact that improved productivity, yield, and selectivity characteristics as to the end products are attained in the proposed process alongside with a considerably reduced temperature of the dehydrogenation process (160° to 340° C. instead of 375° to 400° C. in the known process), which saves power and thus renders the process involved still more economical.

The proposed process for dehydrogenating oxygen-containing derivatives of the cyclohexane series is featured by simple processing techniques and may be carried into effect on standard process equipment.

DETAILED DISCLOSURE OF THE INVENTION

The herein-proposed catalyst is prepared according to common techniques by impregnating powdery contact carriers, such as silica, diatomite, silicon carbide, or magnesia, with nickel and tin salts in an aqueous medium or in organic polar solvents, e.g., alcohols, amines, dialkylsulphates, dialkylsulphoxides, or various combinations thereof.

Any of the aforesaid contact carriers may be used as an inert catalyst support, provided they have a sufficiently developed specific surface, e.g., from 2 to 250 $m^2/g$, featuring pore size from 10 to 1000 Å.

Used as nickel and tin salts may be any organic or inorganic salts decomposable at a temperature not above 400° C. Thus, there may be used for the purpose chlorides, nitrates and sulphates of the said metals, or their ammonia complexes, as well as formates, acetates, propionates of these metals, or their salts of some other acids.

Once the inert carrier has been impregnated with the solutions of the abovesaid nickel and tin salts in the afore-mentioned solvents at a temperature of from 10° to 100° C. and the mixture has been stirred for 12 to 70 hours, said mixture is dried for 2 to 3 hours at 80° to 120° C. and then calcined at 400° to 500° C. for 3 to 5 hours. Then the thus-prepared powdery catalyst is shaped into 1 to 3 mm pellets, the latter are charged into a tubular flow reactor and reduced with a hydrogen-containing gas at a temperature gradually rising to 400° to 450° C., whereupon the catalyst is held at that temperature for 2 to 6 hours, the hydrogen pressure ranging from 0.2 to 20 atm.

An alternative process for preparing the present catalyst may be resorted to, which consists in applying volatile nickel and tin compounds to a preshaped inert carrier by adsorbing said components by the inert carrier from a gaseous phase. Used as volatile nickel compounds may be, say, nickel carbonyl or $\pi$-allyl complexes of nickel, while employed as volatile tin compounds may be such ones as tin tetrachloride, or some organo-tin compounds, e.g., tin tetramethide, tin tetrapropyl, etc.

Application of organic or carbonyl nickel compounds, and organic or inorganic tin compounds for the catalyst preparation makes it possible to do away with calcining supported nickel and tin compounds in the atmospheric air, while finished catalyst may be prepared by reducing carbonyl or organic nickel compounds and organic or inorganic tin compounds with hydrogen at elevated temperatures immediately after said compounds have been adsorbed on a carrier. Reduction of the nickel and tin compounds runs in a stream of hydrogen at 20° to 450° C. and a hydrogen pressure of from 0.2 to 20 atm.

The thus-prepared catalyst is blown through with an inert gas, nitrogen or carbon-dioxide gas at a reduction temperature for 15 to 30 minutes, whereupon the temperature is decreased to within 160° and 340° C., and catalytic dehydrogenation of oxygen-containing derivatives of the cyclohexane series (i.e., the original stock) is carried out over the thus-obtained catalyst.

Used as said oxygen-containing derivatives of the cyclohexane series may be such as cyclohexanol, cyclohexanone, alkyl-derivatives of cyclohexanol and cyclohexanone, e.g., methyl-, butyl- and tert-butylcyclohexanol, cyclohexanediol-1,3, cyclohexanediol-1,4, cyclohexanetriols, 2-hydroxycyclohexanone, cyclohexanedione-1,2, cyclohexanedione-1,4, alkyl-substituted cyclohexanediols, e.g., tert-butylcyclohexanediol-1,2, ethylcyclohexanediol-1,2, etc.

The herein-proposed process for dehydrogenating oxygen-containing derivatives of the cyclohexane series consists in that fed into a tubular flow reactor provided with an evaporator situated before the catalyst bed, after having reduced the catalyst, are the vapours of the original stock preliminarily diluted to a pressure of from 0.003 to 0.1 atm with an inert gas, aliphatic hydrocarbons $C_1$-$C_4$, nitrogen, carbon-dioxide gas, steam, aliphatic alcohols $C_1$-$C_3$, or various combinations thereof, e.g., a mixture of steam and carbon-dioxide gas, a mixture of steam and methane, a mixture of nitrogen and aliphatic hydrocarbons $C_1$-$C_4$, the dehydrogenation temperature ranging between 160° and 340° C. Dehydrogenation may be carried out at any pressure, though most reasonable is to use a pressure approximating the atmospheric one.

When there are used as original stock compounds soluble in water or in said aliphatic alcohols, said compounds are expediently fed into the reactor as their solutions in said solvents, which upon evaporating in the reactor (evaporator) serve as diluents.

In the case of gaseous diluents, used as an original stock are compounds that are either liquids or solid compounds under STP conditions; in the latter case they are to be melted beforehand, e.g., cyclohexanediols and their derivatives. Such being the case, the original stock is fed into the reactor by bubbling the gaseous diluent through the liquid or molten stock, or the stock is fed separately (as fine liquid drops) from the gaseous diluent.

The reaction mixture leaving the reactor after having been contacted with the catalyst, is caught in traps at a temperature of from minus 78° to plus 20° C. The thus-obtained catalysate is homogenized by adding ethanol or some other solvent thereto, whereupon the solution is analyzed chromatographically (GLC) using a flame-ionization detector. The chromatographic column contains 10 percent of Lukooil DF on Chromaton NAW, the column temperature being within 100° and 160° C. and the rate of helium flow, 40 ml per minute. In addition, in order to carry out physico-chemical analyses of the reaction products, organic compounds are extracted from water with carbon tetrachloride, butanol, butylacetate, etc., while pure compounds are isolated by distilling the extracts after evaporation of the solvent. The structure of the end products is identified using spectral characteristics (UV-spectra), qualitative tests for individual functional groups, as well as ultimate analysis.

For a better understanding of the present invention, the following examples of its practical embodiment are given hereinbelow by way illustration, the effective catalyst operating time in said examples being six hours unless otherwise stated.

EXAMPLE 1

There is prepared a catalyst of the following weight percentage composition:
nickel—55
tin—1.95
diatomite—43.05
The atomic ratio of Ni:Sn equals 57:1.

To 10 kg diatomite having a specific surface of 90 $m^2/g$ there is poured 25 ml aqueous nickel nitrate solution, containing 18.8 g nickel, the mixture is stirred for 2 hours at 20° C. and held for 20 hours, whereupon water is evaporated to a paste-like state. Poured to the thus-obtained paste under stirring is 20 ml aqueous stannous chloride, containing 0.45 g tin, the mixture is held for 24 hours at 20° C., whereupon water is evaporated to a paste-like state. The thus-obtained paste is dried at 110° to 120° C. in the air for 2 hours, shaped into pellets (3 mm in diameter and 1 mm thick), calcined at 400° C. for 3 hours in a stream of moist air (1 percent moisture content), and cooled down to yield the desired catalyst in an oxidized form.

Then the oxidized catalyst (5 ml) is charged into the reactor, which is essentially a dia. 13 mm quartz tube provided with a porous partition for the charged catalyst to accommodate, whereupon 20 ml crushed quartz is charged above the catalyst bed to provide better conditions for stock evaporation. The oxidized nickel-tin catalyst is reduced in a stream of hydrogen diluted with nitrogen (volume ratio 1:5), at a temperature gradually rising from 20° to 400° C. (for 2 hours) then with pure hydrogen (10 l/h) at 400° C. for 3 hours. According to evidence obtained by X-ray diffraction analysis, ultimate analysis and atomic-absorption spectroscopy, complete reduction of the nickel and tin compounds to metals occurs under the abovesaid conditions, the thus-reduced catalyst having the composition specified above.

The thus-reduced catalyst is blown with nitrogen for 15 minutes at 400° C., whereupon the temperature of the nitrogen flow is reduced to 160° C., and catalytic dehydrogenation of cyclohexanol is carried out.

To this end cyclohexanol is fed from a dropping funnel to the reactor preheated to 160° C. at an space velocity of 4 kg/l.hr, as well as a mixture of steam and nitrogen (volume ratio 1:1) at a rate of 44 $m^3/l.hr$, the partial pressure of cyclohexanol being 0.02 atm. After having been in contact with the catalyst the reaction products are caught in two traps at 20° C. and −78° C. Every 30 minutes the catalysate from the traps is homogenized by adding 50 percent of ethanol thereto, and is subjected to chromatography at a column temperature of 100° C. The chromatographic evidence demonstrate the catalysate to consist of the following components (wt. %): cyclohexanone; 60; cyclohexene, 6; cyclohexanol, 34. The conversion of the stock makes up 66 percent, selectivity and productivity for cyclohexanone, being 90.9 wt. % and 2.40 kg/l per hour, respectively. The afore-stated characteristics remain unaffected within a continuous operation of the catalyst for 240 hours.

EXAMPLE 2

There is prepared a catalyst of the following weight percentage composition:
nickel—55
tin—0.27
diatomite—44.73
The atomic ratio of Ni:Sn is 410:1.

The catalyst is prepared following the technique of Example 1, with an exception that added to the nickel-diatomite catalyst paste is 20 ml of a solution of stannous chloride dihydrate in dimethylformamide, containing 0.08 g tin. The mixture is stirred for 2 hours at 20° C., held for 20 hours and the solvent is evaporated in vacuo at 80° C. for 3 hours. The resultant powder is shaped into pellets (3×1 mm) and calcined at 450° C. for 3 hours in a stream of moist air (1 percent moisture content) to obtain the desired catalyst in an oxidized state.

Then the oxidized catalyst (5 ml) is charged into the reactor to be reduced there as in Example 1 at 400° C. for 2 hours. According to evidence obtained from the aforesaid analyses the thus-reduced catalyst has the composition specified above.

The reduced catalyst is cooled down to 180° C. in a stream of helium, whereupon the catalytic cyclohexanol dehydrogenation is performed according to the techniques described in Example 1. The feed rate of the stock is 4.0 kg/l per hour, that of steam, 8.0 m³/l per hour. The experiment takes 6 hours to run. The reaction mixture is condensed as described in Example 1, and the homogenized catalyzate is subjected to chromatography at a column temperature of 100° C. Chromatographic evidence thus obtained shows the catalysate to consist of the following components (wt.%): cyclohexanone, 85; cyclohexene, 5; cyclohexanol, 10. The conversion of cyclohexanol makes up 90 percent, selectivity and productivity for cyclohexanone, 94.4 percent and 3.4 kg/l per hour, respectively.

EXAMPLE 3

There is prepared a catalyst of the following weight percentage composition:
nickel—25
tin—1.9
silica—73.1
The atomic ratio of Ni:Sn is 26.6:1.

Poured into 20 g silica in the form of powder having the particle size of from 10 to 50 μm and specific surface of 25 m²/g is 50 ml aqueous nickel chloride hexahydrate containing 6.9 g nickel. The mixture is stirred 2 hours at 20° C., held 20 hours, whereupon water is evaporated at 90° C. to obtain a paste. Then 40 ml aqueous stannous chloride containing 0.55 g tin, is poured to the resultant paste. The mixture is stirred for 2 hours, held for 6 hours at 25° C., whereupon water is evaporated. The resultant paste is dried at 100° C. in the air for 2 hours, shaped into pellets sized 3×1 mm and calcined at 400° C. for 5 hours in a stream of moist air (1 percent moisture content) to obtain the desired catalyst in an oxidized state.

Then 3 ml oxidized catalyst is charged into the reactor to be reduced there as in Example 1 at 400° C. for 2 hours. The reduced catalyst is proved to have the aforespecified composition according to the evidence of the aforesaid analyses.

The reduced catalyst is cooled down to 240° C. in a stream of helium, whereupon catalytic cyclohexanol dehydrogenation is carried out at feed rates of the liquid stock and the diluent (helium) being 3,5 kg/l.hr and 14.9 m³/l.hr, respectively, while the partial pressure of the stock is 0.05 atm. The reaction mixture is condensed, and the catalysate is subjected to chromatography at a column temperature of 100° C. Chromatographic evidence thus obtained demonstrates the catalysate to consist of the following components (wt.%): phenol, 98; cyclohexanol, 0.4; cyclohexanone, 1.6. The conversion of cyclohexanol is 99.6, selectivity and productivity for phenol being 98.4 percent and 3.43 kg/l per hour, respectively.

EXAMPLE 4

There is prepared a catalyst of the following weight percentage composition:
nickel—30
tin—0.2
magnesia—69.8
The atomic ratio of Ni:Sn is 303:1.

Poured into 20 g magnesia powder (particle size being of from 10 to 50 μm and specific surface of 40 m²/g) is 40 ml of an aqueous solution containing 8.7 g nickel and 0.065 g tin in the form of chlorides thereof. The resultant mixture is stirred for 2 hours and held for 24 hours at 20° C., whereupon water is evaporated at 90° C. to obtain a paste, which is then dried at 110° C. in the air for 3 hours, shaped into pellets sized 3×1 mm and calcined at 450° C. in a stream of moist air to obtain the desired catalyst in an oxidized state.

Then 3 ml oxidized catalyst is charged into the reactor to be reduced there as in Example 1 at 400° C. for 3 hours. As evidenced by the afore-mentioned analyses the composition of reduced catalyst is such as above.

The reduced catalyst is cooled down to 300° C. in a stream of methane fraction (the methane content is about 95 vol.%, the rest being higher homologues of $C_2-C_4$), whereupon catalytic cyclohexanone dehydrogenation is performed, feed rates of the liquid stock and diluent (the aforesaid methane fraction) being 2.0 kg/l.hr and 4.0 m³/l.hr, respectively, while the partial pressure of the stock is 0.1 atm. The reaction mixture is condensed in two traps at a temperature of plus 20 and minus 78° C., and the catalysate is subjected to chromatography at a column temperature of 100° C. The chromatography thus carried out evidences the catalysate to consist of the following components (wt.%): phenol, 99; cyclohexanone, 1. The conversion of cyclohexanone equals 99, selectivity and productivity for phenol being 100 percent and 1.98 kg/l per hour, respectively.

EXAMPE 5

There is prepared a catalyst of the following weight percentage composition:
nickel—15
tin—1.95
silicon carbide—83.05
The atomic ratio of Ni:Sn is 15.6:1.

Poured into 20 g silicon carbide powder (particle size being of from 10 to 50 μm and specific surface of 4 m²/g) is 40 ml of an aqueous solution containing 3.7 g nickel and 0.48 g tin in the form of chlorides thereof. The mixture is treated, shaped and reduced as in Example 4 to obtain the desired catalyst of the aforesaid composition.

The reduced catalyst is cooled down to 180° C. in a stream of carbon-dioxide gas, whereupon catalytic dehydrogenation of cyclohexanediol-1,2 is carried out. The feed rates of the premelted stock, steam and carbon-dioxide gas equal 1.0 kg/l.hr, 2.0 and 2.0 m³/l.hr, respectively, the partial pressure of cyclohexanediol-1,2 being 0.05 atm. The reaction mixture is condensed in two traps at a temperature of minus 20 and plus 20° C. The resultant liquid catalysate is homogenzied by adding 50 vol.% of ethanol thereto, and is subjected to chromatography at a column temperature of from 100° to 155° C. (programmed heating). The chromatography thus carried out evidences the catalysate to consist of the following components (wt.%): 2-hydroxycyclohexanone, 48; pyrocatechol, 12; cyclohexanediol-1,2,40. The presence of 2-hydroxycyclohexanone in the catalysate is identified after its having been isolated by recrystallization from an aqueous ethanol (70 vol.%), by IR- and UV-spectroscopy techniques. The IR spectrum shows the absorption band near 3470 and 1720 cm$^{-1}$; the UV spectrum demonstrates absorption near 263 nm. In addition, 2-hydroxycyclohexanone isolated from the catalyzate is capable of reacting with the ion of tervalent bismuth (which is characteristic of the acyloin group —CO—CH(OH)—), accompanied by falling of metallic bismuth into precipitate.

The conversion of cyclohexanediol-1,2 is 60, selectivity and productivity 2-hydroxycyclohexanone being 80 percent and 0.48 kg/l per hour, respectively, while selectivity for pyrocatechol is 20 percent.

EXAMPLE 6

There is prepared a catalyst of the following weight percentage composition:
nickel;13 50
tin—1.8
silica—48.2
The atomic ratio of Ni:Sn is 56.5:1.

Charged into a stainless-steel tubular reactor is 3 g silica (particle size being of from 0.5 to 2 mm and specific surface of 200 m²/g), whereupon the reactor is heated to 300° C. Then passed through the silica bed is a stream of nickel carbonyl vapours, resultant from treating the nickel foil weighing 3.8 g with carbon monoxide at 180° C. Once the nickel foil has been consumed nearly completely, with takes 5 to 6 hours the communicating pipes and the reactor are blown through with helium for 10 minutes. Then fed into the reactor at 300° C. is tin tetramethide, by bubbling helium into a solution of 0.22 g tin tetramethide in anhydrous benzene for 2 hours. Upon terminating the feed of tin tetramethide hydrogen is added to the reactor to attain a pressure of 10 atm, whereupon silica support carrying nickel and tin deposited upon it is hydrogen-treated at the aforesaid pressure and a temperature of 300° C. for 3 hours. After such a treatment the evidence of electron diffraction analysis and atomic-absorption spectroscopy demonstrate the catalyst to comprise metallic nickel and tin and to have the aforesaid composition.

The reduced catalyst is cooled down to 200° C. in a stream of nitrogen, and catalytic dehydrogenation of cyclohexanediol-1,2 is carried out, the stock being fed into the reactor as a 10-percent aqueous solution of cyclohexanediol-1,2. The feed rate of the aqueous solution is 8 kg/l.hr, including stock feed rate of 0.8 kg/l.hr. The partial pressure of stock is 0.1 atm.

The reaction mixture is treated and analyzed as in Example 5. The chromatography carried out evidences the catalysate to consist of the following components (wt.%): pyrocatechol, 54; 2-hydroxycyclohexanone, 36; cyclohexanediol-1,2, 10. The presence of pyrocatechol in the catalysate is identified by formation of precipitate on adding a solution of lead acetate in ethanol to the catalysate. The weight of the dry residue corresponds to the pyrocatechol content of the catalysate as determined chromatographically.

The conversion of cyclohexanediol-1,2 is 90, selectivity and productivity for pyrocatechol being 60 percent and 0.43 kg/l per hour, respectively, while selectivity for 2-hydroxycyclohexanone is 40 percent.

EXAMPLE 7

There is prepared a catalyst of the following weight percentage composition:
Nickel—15
tin—0.2
diatomite—84.8.
The atomic ratio of Ni:Sn is 121:1.

Poured to 20 g diatomite (particle size being of from 10 to 50 μm, specific surface, 90 m²/g) is 50 ml of a solution of nickel nitrate hexahydrate in ethanol, containing 3.75 g nickel, and stannous chloride dihydrate, containing 0.05 g tin. The mixture is stirred for 2 hours at 100° C. till a paste results. The thus-obtained paste is treated, shaped and reduced as in Example 4 to produce the desired catalyst of the aforesaid composition.

Fed into the reactor containing 3 ml of the reduced catalyst featuring the aforesaid composition at 240° C. is a solution of 2-hydroxycyclohexanone (5 mol.%) in ethanol, the feed rate being 9.13 kg/l per hour, while the feed rate of the stock is 1.16 kg/l per hour, and the partial pressure of the stock is 0.05 atm. The reaction mixture is condensed in two traps at a temperature of minus 20 and plus 20° C. to obtain an alcoholic catalyzate solution. The catalysate is subjected to chromatography at 100° to 155° C., which evidences the catalysate to consist of the following components (wt.%): pyrocatechol, 95; phenol, 5. The conversion of 2-hydroxycyclohexanone is 100, selectivity and productivity for pyrocatechol being 95 percent and 1.1 kg/l per hour, respectively.

EXAMPLE 8

A catalyst is prepared according to the techniques of Example 2, having the following weight percentage composition:
nickel—54
tin—0.27
diatomite—45.6
dipotassium hydrogen phosphate—0.13
The atomic ratio of Ni:Sn is 404:1.

The only difference of the catalyst preparation procedure from that of Example 2 resides in that the nickel-diatomite catalyst paste is treated with 20 ml of a solution of stannous chloride dihydrate and dipotassium hydrogen phosphate ($K_2HPO_4$) in dimethylsulphoxide, said solution containing 0.08 g tin and 0.04 g $K_2HPO_4$. The mixture is treated, shaped and calcined as in Example 2.

Then 3 ml of the thus-prepared catalyst in an oxidized form is charged into the reactor to be reduced there at 400° C. for 3 hours. Upon being subjected to the aforesaid analyses the reduced catalyst is evidenced to have the aforesaid composition.

Next the reduced catalyst is cooled down to 300° C. in a stream of helium, and catalytic dehydrogenation of cyclohexanediol-1,2 is carried out over the catalyst thus prepared. The stock is fed into the reactor as a 10-percent aqueous solution at a rate of 1.16 kg/l.hr, while the partial pressure of the stock is 0.017 atm.

The reaction mixture is treated and analyzed as in Example 5. The chromatography thus carried out evidences the catalysate to consist of the following components (wt.%): pyrocatechol, 97; phenol, 3. The desired pyrocatechol is isolated from the reaction mixture, comprising water, by extraction with butanol. Once the solvent has been distilled off there is obtained pyrocatechol which is pure to above 99.5 percent and features its boiling point (240° C. at 760 mm Hg) and melting point (105° C.) do not differ from those known in literature. The conversion of cyclohexanediol-1,2 equals 100, while selectivity and productivity for pyrocatechol are 97 percent and 1.13 kg/l per hour, respectively.

EXAMPLE 9

A catalyst is prepared according to the techniques of Example 3, having the following weight percentage composition:
nickel—54
tin—1.1
silica—44.89
sodium sulphide—0.01
The atomic ratio of Ni:Sn is 99:1.

The only specific feature of the catalyst preparation procedure from that of Example 3 consists in adding 2.1 mg sodium sulphide to an aqueous stannous chloride solution and in mixing said solution with diatomite-based nickel paste. The mixture is treated, shaped and calcined as in Example 3.

Then 3 ml of the thus-prepared catalyst in an oxidized form is charged into the reactor to be reduced there with hydrogen at 450°C. for 2 hours. As evidenced by the afore-mentioned analyses the reduced catalyst has the above-specified composition.

The reduced catalyst is cooled down to 310° C., and catalytic dehydrogenation of 4-ethylcyclohexanediol-1,2 is carried out. The stock is fed into the reactor as a 1 mol.% solution in methanol at rate of 2.32 kg/l.hr, the partial pressure of the stock being 0.01 atm.

The reaction mixture is treated and analyzed as in Example 7. The chromatography carried out evidences the catalysate to consist of the following components (wt.%): 4-ethylpyrocatechol, 95; phenol, 5. The conversion of 4-ethylcyclohexanediol-1,2 equals 100 percent, while selectivity and productivity for 4-ethylpyrocatechol are 95 percent and 2.2 kg/l per hour, respectively.

EXAMPLE 10

A catalyst is prepared according to the techniques of Example 8, having the following weight percentage composition:
nickel—54
tin—1.0
silica—44.2
sodium sulphate—0.8.
The atomic ratio of Ni:Sn is 99:1.

The only feature distinguishing the catalyst preparation procedure from that of Example 8 is the substitution of $Na_2SO_4$ for $K_2HPO_4$ in the impregnation solution.

Then 3 ml of the thus-prepared catalyst is heated to 340° C. in a stream of nitrogen, and catalytic dehydrogenation of cyclohexanediol-1,4 is carried out. The stock is fed into the reactor as a 10-percent aqueous solution at a rate of 3.5 kg/l.hr. In addition, nitrogen is fed into the reactor at a rate of 27.3 $m^3$/l.hr, the partial pressure of the stock being 0.01 atm.

The reaction mixture is treated and analyzed as in Example 5. The chromatography carried out evidences the catalysate to consist of the following components (wt.%): hydroquinone, 87; phenol, 13. The conversion of cyclohexanediol-1,4 equals 100, while selectivity and productivity for hydroquinone are 87 percent and 3.03 kg/l per hour, respectively.

EXAMPLE 11

A catalyst is prepared according to the techniques of Example 3, having the following weight percentage composition:
nickel—54
tin—1.1
diatomite—43.9
lithium chloride—1.0.
The atomic ratio of Ni:Sn is 106.:1.

Then 3 ml of the catalyst is heated to 330° C. in a stream of helium, and catalytic cyclohexanone dehydrogenation is carried out, the stock being fed into the reactor at a rate of 4.8 kg/l.hr. Besides, stream is fed into the reactor at a rate of 9.6 $m^3$/l.hr, the partial cyclohexanone pressure being 0.1 atm.

The reaction mixture is treated and analyzed as in Example 3. The chromatography carried out evidences the catalysate to consist of the following components (wt.%): phenol, 78.5; resins containing 2 or 3 cyclohexane rings, 1.5; cyclohexanone, 20. The conversion of cyclohexanone equals 80, while selectivity and productivity for phenol are 98 percent and 3.76 kg/l per hour, respectively.

EXAMPLE 12

Use is made of the catalyst as prepared in Example 5 and having the following weight percentage composition:
nickel—15
tin—1.95
silicon carbide—83.05.
The atomic ratio of Ni:Sn is 15.6:1.

The reduced catalyst (3 ml) is heated to 270° C. in a stream of nitrogen, and catalytic dehydrogenation of 4-tert-butylcyclohexanediol-1,2 is carried out. The stock is fed into the reactor as a 5 mol.% solution in ethanol at a rate of 1.16 kg/l.hr, the partial pressure of the stock being 0.05 atm.

The reaction mixture is treated and analyzed as in Example 7. The chromatography carried out evidences the product to consist of the following components (wt.%): 4-tert-butyl-2-hydroxycyclohexanone, 92; 4-tert-butylcyclohexanediol-1,2, 8. The conversion of stock equals 92, while selectivity and productivity for 4-tert-butyl-2-hydroxycyclohexanone are 100 percent and 1.07 kg/l per hour, respectively.

EXAMPLE 13

Use is made of the catalyst as prepared in Example 2 and having the following weight percentage composition:
nickel—55
tin—0.27
diatomite—44.73
The atomic ratio of Ni:Sn is 410:1.

The reduced catalyst (3 ml) is heated to 220° C. in a stream of nitrogen, and catalytic dehydrogenation of cyclohexanedione-1,2 is carried out. The liquid stock is fed into the reactor at a rate of 0.795 kg/l.hr, while nitrogen is fed at a rate of 53 $m^3$/l.hr and the partial pressure of the stock is 0.003 atm.

The reaction mixture is condensed in two traps at a temperature of minus 20 and plus 20° C. The catalysate is subjected to chromatography at a column temperature of 140° C. The chromatography thus carried out evidences the catalysate to consist of the following components (wt.%): pyrocatechol, 90; cyclohexanediol-1,2, 10. The conversion of stock equals 90, while selectivity and productivity for pyrocatechol are 100 percent and 0.715 kg/l per hour, respectively.

EXAMPLE 14

Use is made of the catalyst prepared in Example 1. The reduced catalyst (3 ml) is heated in a steam of nitrogen to 180° C., whereupon catalytic dehydrogenation of 3-methylcyclohexanol is carried out. The liquid original stock is fed into the reactor at a rate of 2.3 kg/l.hr, nitrogen, at a rate of 6.7 $m^3$/l.hr, the partial pressure of 3-methylcyclohexanol being 0.067 atm.

The reaction mixture is condensed in two traps at a temperature of minus 20 and plus 20° C. The catalysate is subjected to chromatography at a column temperature 120° C. The chromatography thus carried out evidences the catalysate to consist of the following components (wt.%): 3-methylcyclohexanone, 85; 3-methylcyclohexanol, 15. The conversion of stock equals 85, while selectivity and productivity for 3-methylcyclohexanone are 100 percent and 1.95 kg/l per hour, respectively.

EXAMPLE 15

Use is made of the catalyst as prepared in Catalyst 1 and having the following weight percentage composition:
nickel—55
tin—1.95
diatomite—43.05.
The atomic ratio of Ni:Sn is 57:1.

The reduced catalyst (5 ml) is heated to 270° C. in a stream of nitrogen, whereupon catalytic dehydrogenation of cyclohexanediol-1,2 is carried out. The stock is fed into the reactor as a 10-percent aqueous solution at a rate of 1.16 kg/l.hr (the feed rate of the solution being 11.6 kg/l kg/l.hr) and the partial pressure of the stock, 0.017 atm. The process runs continuously for 400 hours, the liquid catalysate being sampled periodically from the trap cooled to 0° C. The catalysate is subjected to chromatography at a column temperature of from 110° to 150° C. (programmed heating). The chromatography of a sample taken on the 6th hour of the catalyst operation demonstrates the catalysate to consist of the following components (wt.%): pyrocatechol, 96; phenol, 4, while the catalysate sample taken on the 400th hour of the catalyst operation features the following weight percentage composition: pyrocatechol, 95; phenol, 4; 2-hydroxycyclohexanone, 1. The conversion of cyclohexanediol-1,2 equals 100, while selectivity and productivity for pyrocatechol are 95 to 96 percent and 1.1 kg/l per hour, respectively. Isolation of pyrocatechol from the catalysate, which is in fact an aqueous solution of organic substances, is effected by two fold extraction with carbon tetrachloride taken in an equal quantity with respect to the catalysate volume. Once the solvent has been distilled off from the extract there is obtained pyrocatechol, which is pure to above 99 percent and features boiling and melting points not differing from those known in the literature.

What is claimed is:

1. A catalyst for dehydrogenating oxygen-containing derivatives of the cyclohexane series having the following general formula

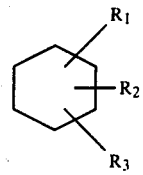

where
$R_1$ is a radical selected from the group, containing hydrogen and alkyls $C_1$-$C_4$,
$R_2$ and $R_3$ are radicals selected from the group, containing —H, —OH, and =O but $R_2$ and $R_3$ cannot both be hydrogen;
$R_1$, $R_2$ and $R_3$ being linked to different carbon atoms of the ring, into the corresponding cyclic organic compounds selected from the group containing cyclic ketones and phenols, and mixtures thereof, said catalyst comprising an active component, -nickel, a promotor -tin, both as free metals, and an inert carrier selected from the group consisting of silica, diatomite, silicon carbide and magnesia, the amounts of said catalyst components being within the following limits as weight percent:
nickel—15 to 55
tin—0.2 to 1.95
inert carrier—84.8 to 43.05
and wherein the atomic ratio of nickel and tin lies within 26.6:1 and 410:1, respectively.

2. A catalyst as claimed in claim 1, also containing an alkali salt of a mineral acid in an amount of from 0.01 to 1.0 wt.%.

* * * * *